United States Patent
Goodman et al.

(10) Patent No.: US 10,231,720 B2
(45) Date of Patent: Mar. 19, 2019

(54) MODULAR APPARATUS FOR DELIVERY OF FLUID MATERIALS

(71) Applicants: Ethicon, Inc., Somerville, NJ (US); Omrix Biopharmaceuticals Ltd., Rehovot (IL)

(72) Inventors: John Goodman, Ann Arbor, MI (US); Jared Schneider, Raritan, NJ (US); Kenneth M. Tamsula, Perth Amboy, NJ (US); Erez Ilan, Kibbutz Netzer Sereni (IL); Tamara Byk-Tennenbaum, Kiryat Ono (IL); John Anastasiadis, Tinton Falls, NJ (US)

(73) Assignees: Ethicon, Inc., Somerville, NJ (US); Omrix Biopharmaceuticals Ltd., Rehovot (IL)

( * ) Notice: Subject to any disclaimer, the term of this patent is extended or adjusted under 35 U.S.C. 154(b) by 183 days.

(21) Appl. No.: 15/336,997

(22) Filed: Oct. 28, 2016

(65) Prior Publication Data
US 2017/0042523 A1 Feb. 16, 2017

Related U.S. Application Data

(63) Continuation of application No. 14/479,435, filed on Sep. 8, 2014, now abandoned.

(51) Int. Cl.
| | | |
|---|---|---|
| *A61B 17/00* | (2006.01) | |
| *A61M 5/19* | (2006.01) | |
| *A61M 5/315* | (2006.01) | |
| *A61B 90/00* | (2016.01) | |
| *A61B 50/30* | (2016.01) | |

(52) U.S. Cl.
CPC ........ *A61B 17/00491* (2013.01); *A61M 5/19* (2013.01); *A61M 5/31596* (2013.01); *A61B 50/30* (2016.02); *A61B 2017/00495* (2013.01); *A61B 2090/0808* (2016.02)

(58) Field of Classification Search
CPC . A61B 17/00491; A61M 5/19; A61M 5/2066; A61M 5/284; A61M 5/31596; A61M 5/3294; A61M 3/005
See application file for complete search history.

(56) References Cited

U.S. PATENT DOCUMENTS

| | | | | |
|---|---|---|---|---|
| 5,253,785 A * | 10/1993 | Haber | ..... | A61M 5/19 222/135 |
| 5,464,396 A * | 11/1995 | Barta | ..... | A61B 17/00491 604/191 |
| 6,458,095 B1 * | 10/2002 | Wirt | ..... | A61B 17/00491 222/137 |
| 6,610,033 B1 * | 8/2003 | Melanson | ..... | A61B 17/00491 604/181 |
| 2012/0175384 A1 * | 7/2012 | Greter | ..... | A61M 5/19 222/137 |

* cited by examiner

*Primary Examiner* — Bhisma Mehta
*Assistant Examiner* — James D Ponton
(74) *Attorney, Agent, or Firm* — Frost Brown Todd LLC

(57) ABSTRACT

Apparatuses and methods for delivery of fluid materials, particularly multi-part fluid materials, including modular apparatuses in which various components are maintained separately until ready for use. Each fluid component is maintained in a separate housing until mixing of the fluid components is desired. Maintaining components separately until use allows for proper filling, sterilization, packaging and storing until use.

17 Claims, 10 Drawing Sheets

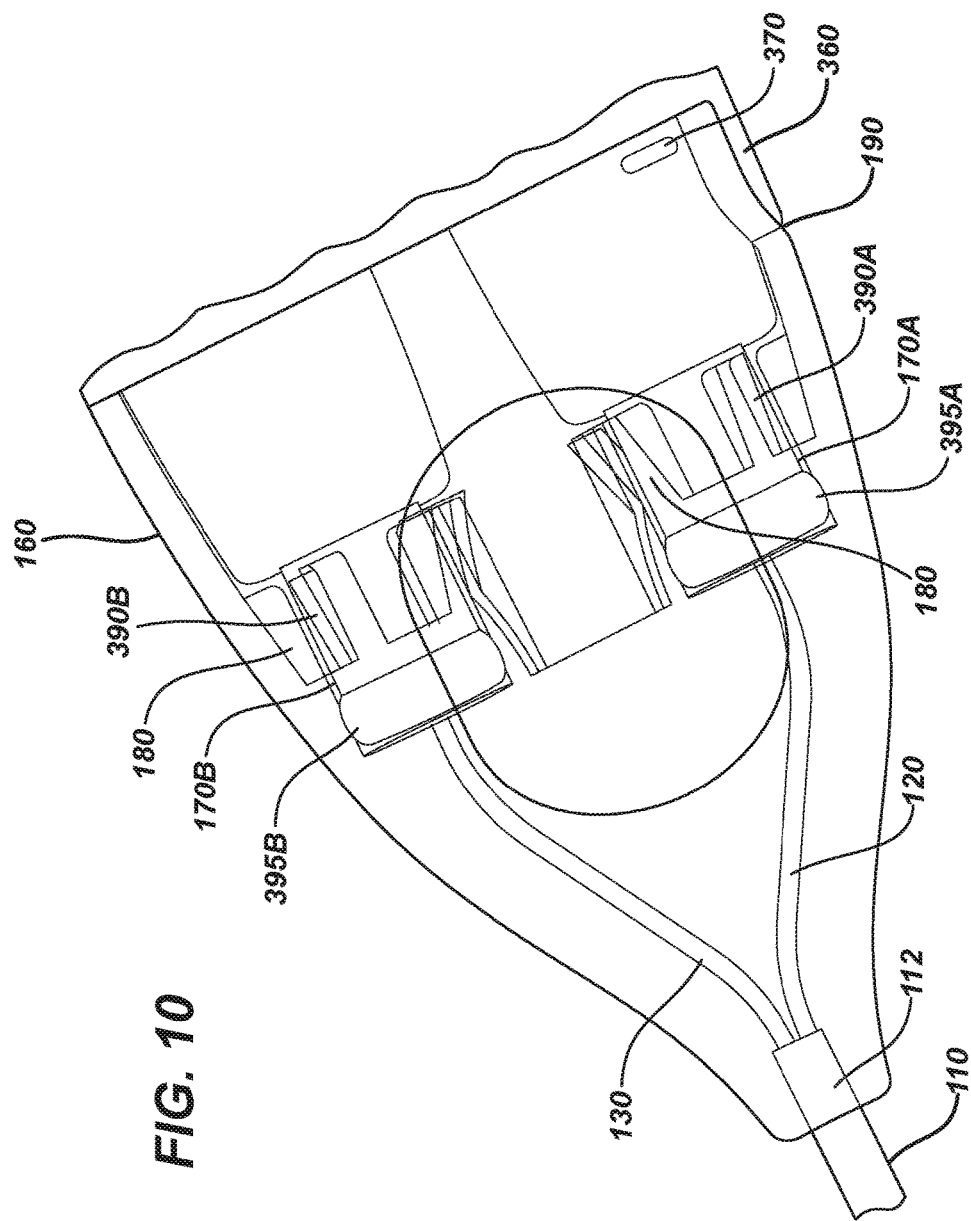

MODULAR APPARATUS FOR DELIVERY OF FLUID MATERIALS

REFERENCE TO RELATED APPLICATIONS

This continuation application claims the benefit of U.S. patent application Ser. No. 14/479,435 entitled: "Modular Apparatus for Delivery of Fluid Materials", filed on Sep. 8, 2014, the contents of which are incorporated by reference in its entirety.

FIELD OF THE INVENTION

The present invention relates to apparatuses and methods for delivery of fluid materials, particularly multi-part fluid materials. The invention maintains each fluid component in a separate housing until mixing of the fluid components is desired. Further, the invention allows for various components to be kept separate until use is desired, and then each component may be assembled quickly and easily to form the applicator.

BACKGROUND

Some biological components, including multi-component materials such as fibrin and its base components (fibrinogen and thrombin), are delicate materials and cannot tolerate processing with conventional sterilization techniques without being significantly compromised or even destroyed when they are in solution. Traditionally, such biological components are manufactured in two packages, the first including a terminally sterilized delivery device, and the second being an aseptically filled vial with non-sterile exterior. While this allows for control of the products, unfortunately the biological materials must then be transferred into the applicator at the time of use. This multi-step process requires some unusual coordination between sterile and nonsterile surgical staff, and may lead to errors or anxiety on the part of that staff. Further, the transfer of materials into a delivery device itself lends itself to potential mistakes and leakage/spillage of material. It would be more desirable for users if the biological products can be delivered in a pre-loaded and sterilized applicator, such that the entire contents could be deposited on the sterile field without the need for further preparation steps.

It is one objective of the present invention to provide a product with this capability to deliver materials pre-loaded and ready for dispensing without filling or loading materials into an applicator. Some two-part materials, such as fibrin sealants, are highly reactive with one another, and it is critical that even the slightest amount of cross-contamination between first and second materials be prevented. Cross-contamination would not only render the device useless, but would require a costly decontamination of the assembly area. To protect against such cross-contamination, it may be desired that each reactive material be loaded and sealed in a separate vessel, and then brought together into a unified device at the time of use without having to transfer the fluid materials into a separate vial or barrel. It is a further objective of the invention to provide for a means of assembly that minimizes potential for cross-contamination.

Further, it is important that the components of the delivery assembly be sterile inside and outside. Even with pre-sterilization of all components entering a filling region, the ability to claim sterility on the exterior of product has traditionally been questionable. It is therefore helpful and is one additional objective of the invention to subject the entire exterior of the device to low level of radiation energy, such as with an electron-beam, after filling with biological or reactive components. This poses a number of unique design challenges, since the exterior surfaces of the device that can be touched by the user, or that come into contact with fluids inadvertently leaked or spilled on the device must be "visible" to the electron beam, since the beam is propagated in a purely linear manner from its source. When such sterilization techniques are used, it is particularly helpful that there be no shadowing, cracks, steps, or crevasses on the device that block line of sight of the beam to these surfaces.

SUMMARY

The invention includes an apparatus for delivery of a biological fluid, particularly a modular apparatus with various components, which may be provided by themselves or all provided together. The delivery device may include an applicator component, the applicator component including: a housing, the housing including a keyfit region; first and second counter bore regions within the housing, each counter bore region having a generally cylindrical shape and being aligned such that the central axes of each counter bore region are parallel with each other; and first and second delivery lumens, each delivery lumen having an insertion end and a delivery end, the insertion end of each lumen including a needled cannula within one of the counter bore regions.

The delivery device also may include a fluid housing component, including: at least two cylindrical barrels having a dispensing end and a plunger receiving end; at least two polymeric caps, where one polymeric cap is fit onto a dispensing end of a cylindrical barrel; a bridge having an open interior, which fits securely on the dispensing end of the at least two cylindrical barrels, the bridge having a keyfit region that fits into the keyfit region of the housing, where securement of the fluid housing component with the applicator component aligns one needled cannula with the interior of one cylindrical barrel by piercing one polymeric cap.

The delivery device may include a plunger component, including: at least two cylindrical plunger components having a first end and second end, each sized such that the first end may be inserted into the plunger receiving end of one of the barrels; an open flange component through which the cylindrical components may be slidably inserted; and a securement feature to secure the dispensing end of the barrels in the open flange component.

The present invention further may include a kit, including at least one of the applicator component, fluid housing component and plunger component. The kit may include at least two of the aforementioned components, or it may include all three components. The kit may further include instructions for use.

The present invention also may include a method of dispensing at least two reactive fluids simultaneously. The method includes the steps of providing an applicator component, providing a fluid housing component and providing a plunger component, securing the applicator component to the fluid housing component, such that each needled cannula pierces one elastomeric cap; securing the plunger component to the fluid housing component; and depressing the plunger, such that each plunger component moves one of the pistons into one of the barrels, thereby forcing each of the first and second biological fluids through one of the delivery lumens.

Another aspect of the invention includes only a fluid housing cartridge for use in a modular delivery device, including at least two cylindrical barrels having an open interior separated by a dispensing end and a plunger receiving end; at least two elastomeric caps, where one elastomeric cap is fit onto the dispensing end of one cylindrical barrel; at least two pistons having a generally cylindrical configuration, with a sealing surface on the outer circumference and a generally flat proximal surface, one piston being placed into the dispensing end of one cylindrical barrel; and a bridge having an open interior, which fits securely on the dispensing end of the at least two cylindrical barrels so as to hold the at least two cylindrical barrels in a substantially parallel configuration.

It may be desired to include a method of sterilizing a pre-filled fluid housing component. The fluid housing component includes at least one barrel, which is filled with a fluid material. The barrel may be sealed by placing a pierceable cap on a distal end of the barrel and fitting a piston within the interior of the barrel at the proximal end of the barrel. The piston is placed in a substantially flush configuration with the proximal end of the barrel, and then the sealed barrel is exposed to sterilization methods, such as radiation energy.

BRIEF DESCRIPTION OF THE FIGURES

FIG. 10 is a close-up view of an applicator component with a see-through housing and a fluid housing component in attached configuration.

DETAILED DESCRIPTION

The present invention relates to a modular delivery device, which includes a plurality of separate components that are capable of being attached to each other and form a resulting fluid delivery assembly. In particular, the delivery device is suitable for delivery of fluid materials, including the simultaneous delivery of a plurality of biological and/or reactable materials that are capable of reacting with each other. For example, one particular combination of materials is fibrinogen and thrombin, which react together to form fibrin. The figures and description herein will refer to a delivery assembly including two barrels, but it is to be understood that the assembly may include only one barrel, or it may include three or more barrels. As will be understood through the description and Figures, for each barrel, there should be a separate fluid lumen, a separate cap, and a separate piston. The delivery of the fluid materials should be simultaneous and allow for mixing at the site and immediately after exiting the device or soon thereafter. The mixing can also be performed within the delivery tube, within the applicator component, or in a specialized mixing tip attached to the delivery tube. If only one barrel is used, the mixing step may be omitted.

With reference to the Figures, a delivery device 10 of the present invention, when fully assembled, includes three components: an applicator component 100, a plunger component 200, and a fluid housing component 300. The invention may include any component separately, or may include multiple components together. The invention further may include a kit, including any one of the three components, any two of the three components, or all three components. The three components are desirably capable of being securely attached to each other, but it may be desired that the components be detachable by a user if detaching is desired. The present invention further relates to methods of assembling and using delivery devices as described below.

Figure 1:
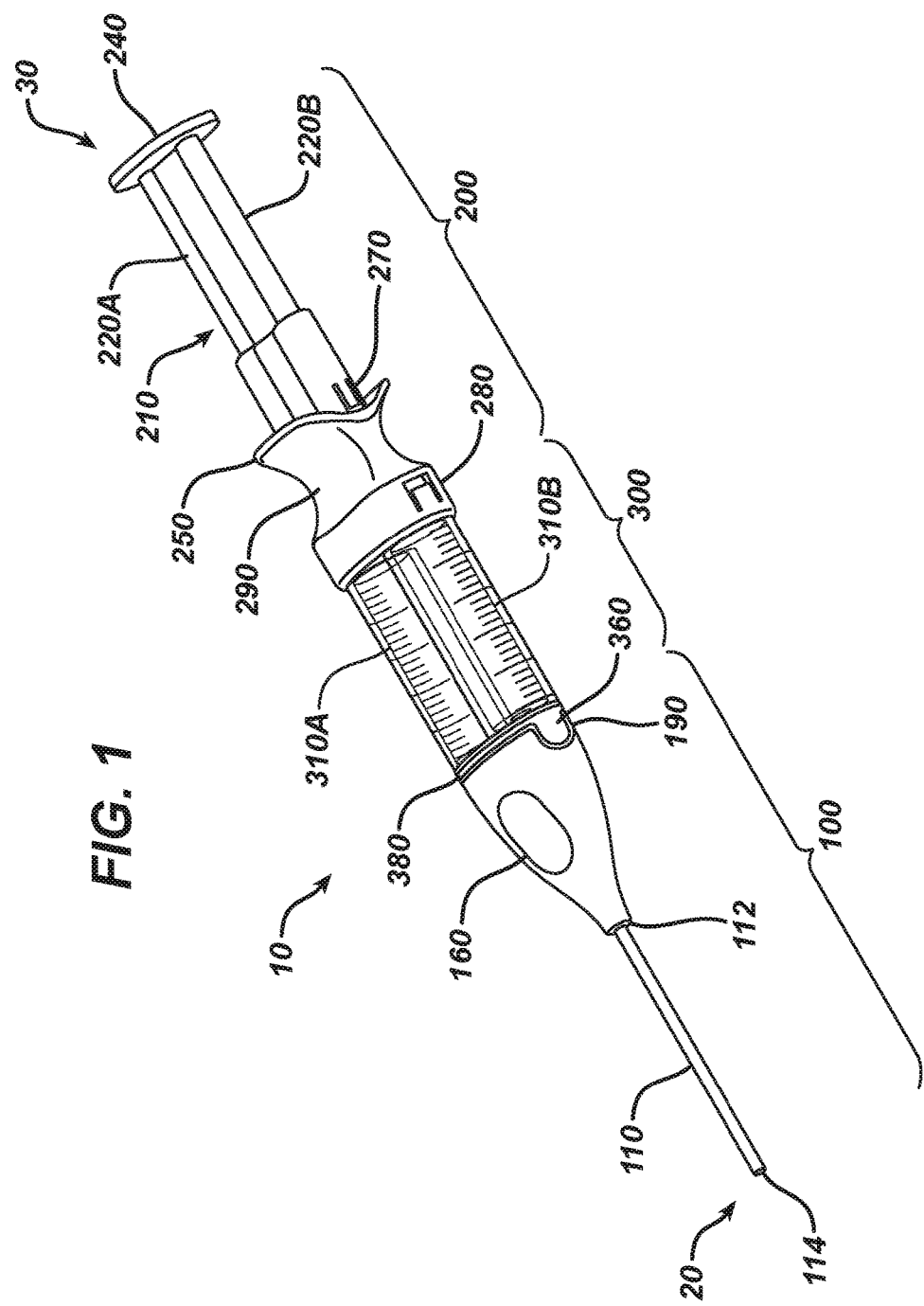
FIG. 1 depicts a view of a delivery apparatus in an assembled configuration.

FIG. 1 shows a fully assembled delivery device 10. As used herein, the term "distal end" refers to the delivery end of the device, e.g., the end that the fluid/fluids leave the device for use. For ease of understanding, the "distal end" of the assembled device is labeled in FIG. 1 as reference numeral 20. The "proximal end" of the delivery device is depicted as reference numeral 30, and refers to the opposite end of the distal end, e.g., the end furthest away from the delivery end of the device, which typically includes a plunger or other device to be manipulated by a user. Throughout the description below, the terms "proximal" and "distal" will refer to the aforementioned sides of the device and each component.

The device 10 includes, at its distal end (20), an applicator component 100. Secured in fluid connection to the applicator component 100 is a fluid housing component 300. Secured to the fluid housing component 300 is a plunger component 200, such that the plunger component 200 is located at the proximal end (30) of the device 10. As can be seen in FIG. 1, when fully assembled, the proximal end of the applicator component 100 is secured to the distal end of the fluid housing component 300, and the proximal end of the fluid housing component 300 is secured to the distal end of the plunger component 200. Each component may be separately formed, sterilized, packaged, and sold, as desired.

One of the aspects of the invention is the ability to form three components separately, subject them to individual sterilization methods, and provide them in a suitable, stabilized format for use by a user. The applicator component 100 and the plunger component 200 are desirably free of fluid materials, such as biological or reactable materials, and thus may be sterilized using conventional methods. The fluid housing component 300 may be provided to users without any materials housed therein, or it may be pre-loaded with the fluid materials to be used. Particularly if the fluid material(s) in the fluid housing component 300 are biological materials, sterilization after loading the fluid materials is important. Although the invention refers to biological fluids, such as fibrin sealants, it may be understood that the present invention is useful for non-biological methods and fluids, such as, for example, two-part epoxy or cyanoacrylate materials. Any multi-part material may be used in the present invention, and for illustrative purposes, the two-part system referenced herein describes delivery of a first fluid and second fluid, such as thrombin and fibrinogen, which, when combined, form fibrin.

Figure 2:
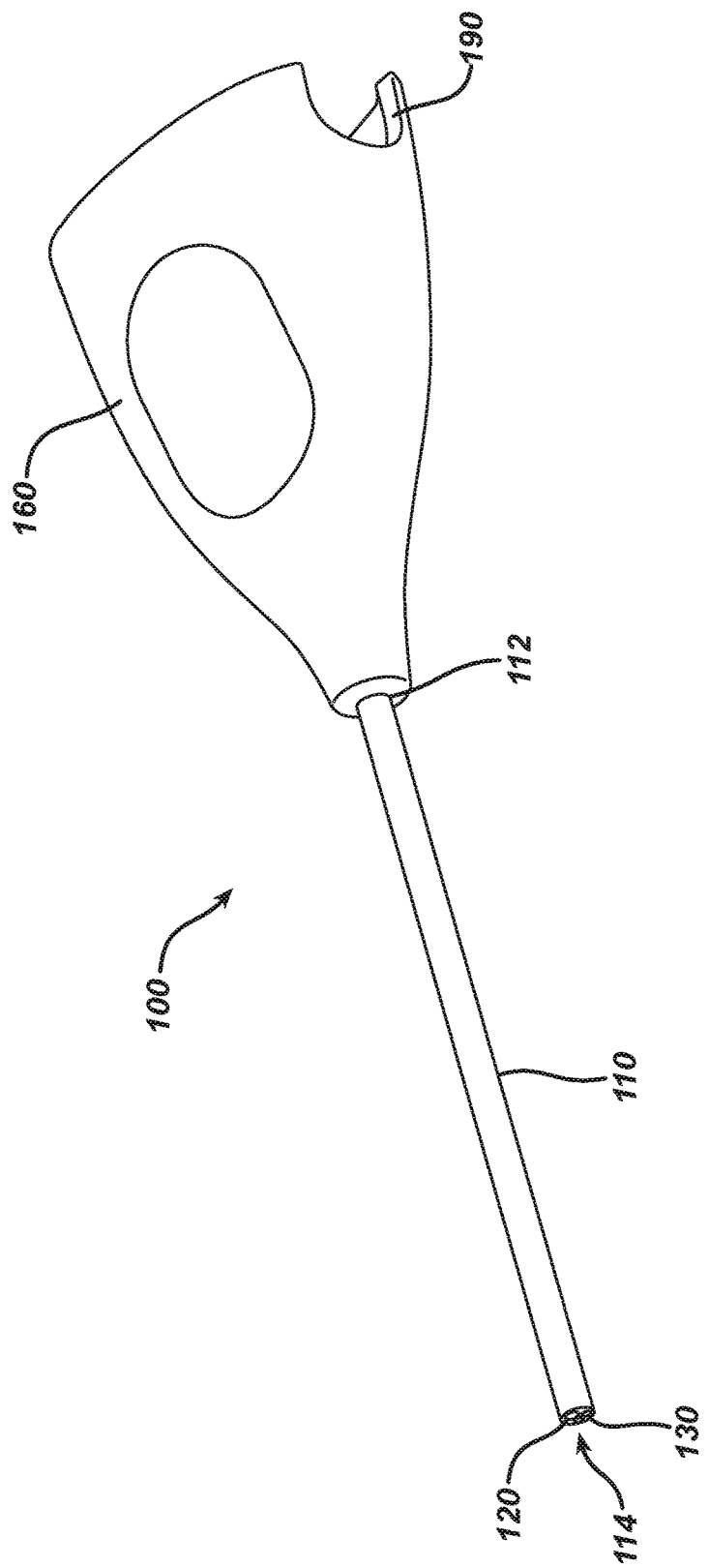
FIG. 2 is a close-up view of an applicator component.
Figure 3:
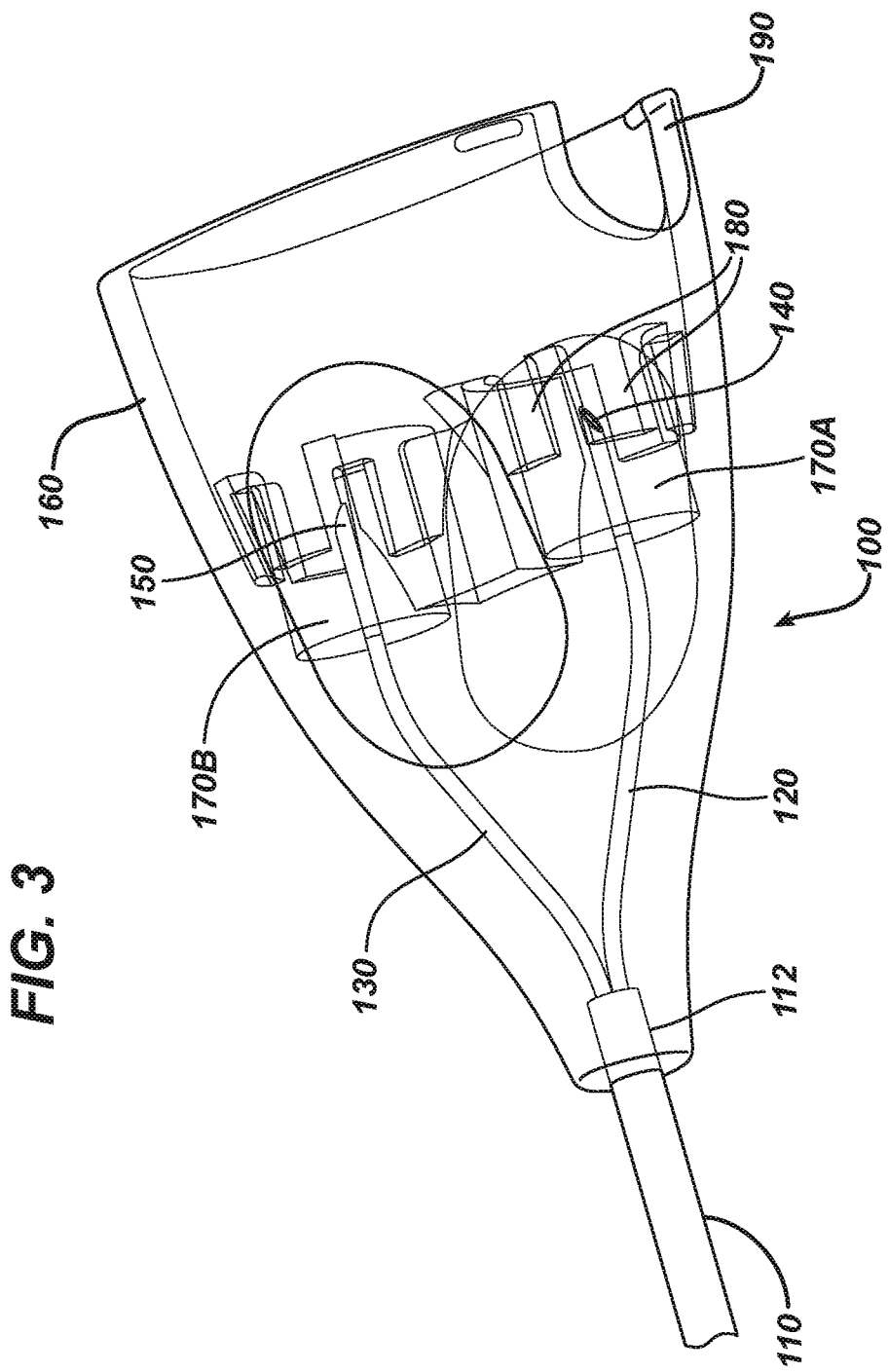
FIG. 3 is a see-through view of the applicator component of FIG. 2.
Figure 4:
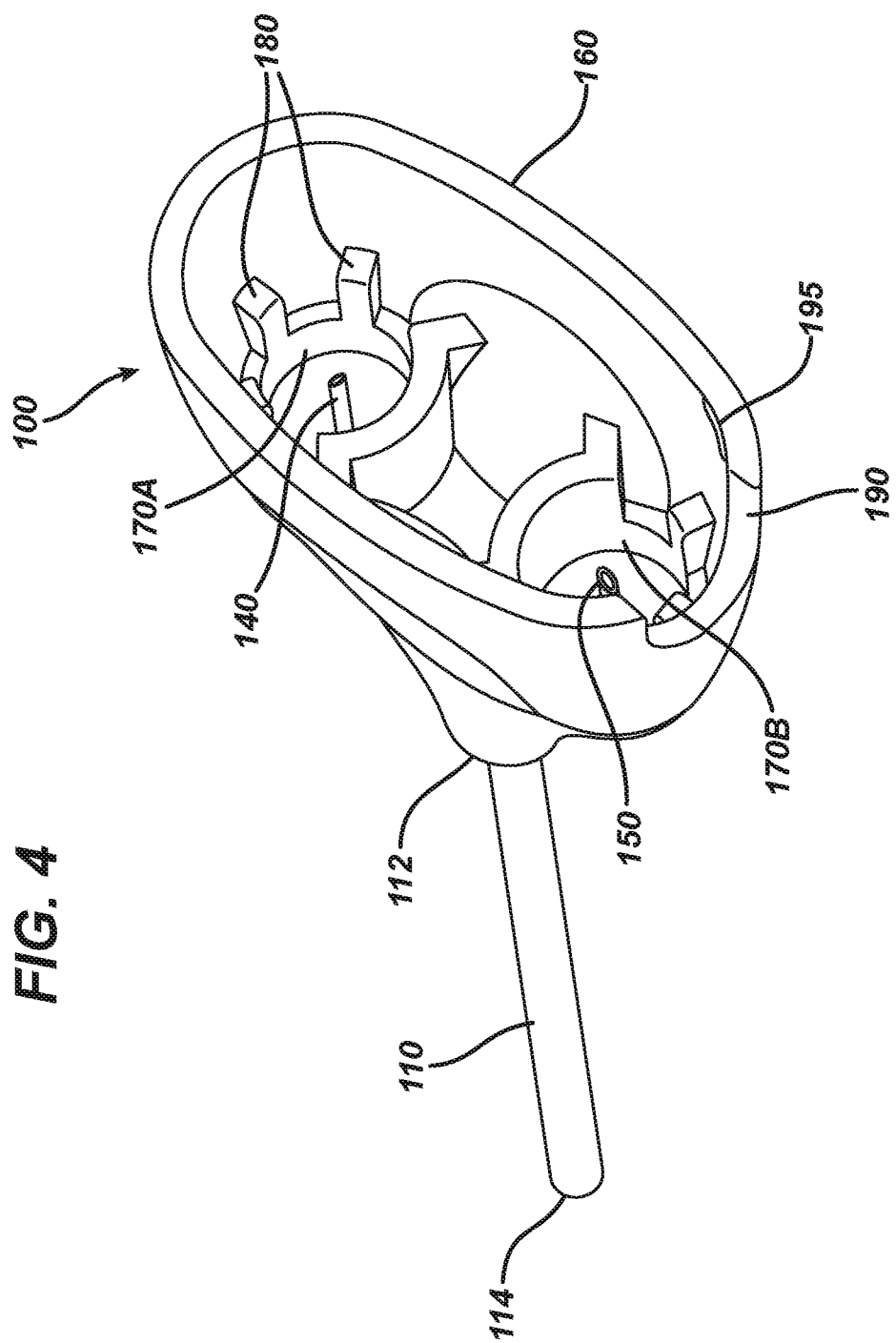
FIG. 4 is a perspective view of the applicator component of FIG. 2.

With reference to FIGS. 2-4, the applicator component 100 is described. The applicator component 100 includes a delivery component, which is any device useful to transport the fluid(s) from the device 10 to the target area. In use, the target area is any site at which the fluid(s) is to be deposited, and in the case of biological sealants, may be a surgical site or the site of a wound. The applicator component may include an elongated tube 110, having a first end 114 (also known as a "distal" or "delivery" end) and a second end 112 located at the "proximal" end of the tube 110. The delivery tube 110 includes at least one internal fluid lumen, and in the case of a two-part delivery device, includes a first fluid lumen 120 and second fluid lumen 130. The first and second fluid lumens 120, 130 run parallel to each other, spanning the entire length of the delivery tube 110. It is important that the fluid lumens 120, 130 remain separated from each other until they reach the delivery site, since premature mixing of the fluid materials may cause undesirable reaction.

The applicator component 100 includes a housing 160, which is essentially hollow and is shaped to provide ergonomic support and use to the end user. It should be noted that a full housing 160 is not required, but is desired. The housing 160 includes a first keyfit feature 190 at its proximal end, which provides the ability to align the applicator component 100 with the fluid housing component 300, as will be described in greater detail below. As used herein, the "keyfit" assembly refers to a first keyfit feature, which is a generally open region, which is sized and shaped to receive a second keyfit feature, which is an outwardly extending region. In the present invention, a first keyfit feature 190 may be found on the housing 160, and a second keyfit feature can be found on the fluid housing component 300.

As can be seen in FIG. 3 (which is the applicator component 100 of FIG. 2, depicted as having a see-through housing 160), the interior of the housing 160 includes the first fluid lumen 120 and second fluid lumen 130, separated from each other. At the proximal ends of the fluid lumens 120, 130 are a first needled cannula 140 and a second needled cannula 150, respectively. The fluid lumens 120, 130 are generally cylindrical and have an open interior. The needled cannula 140, 150 may have any shape desired, with the proviso that the proximal end has a sharpened feature allowing it to pierce a cap, described below. The fluid lumens 120, 130 have an open interior along the entire length from the needled cannula (140, 150) to the distal end 114 of the delivery tube 110.

The needled cannula 140, 150 are located in a fixed configuration in individual open chambers 170A and 170B. Thus, first needled cannula 140 is fixed in place substantially in the center of open chamber 170A, while second needled cannula 150 is fixed in place substantially in the center of open chamber 170B. As can be seen in the Figures, each delivery lumen 120, 130 may be linear as it travels through delivery tube 110, and then may travel along a non-linear path until each arrives at the center of an open chamber 170. Open chambers 170A, 170B are generally cylindrical in shape and are configured to provide a snug fit with fluid delivery caps around the internal surface of the open chambers 170A, 170B. Ribs 180, if used, may be disposed about the periphery of the open chambers 170A, 170B, if desired. The interior of the housing 160 may include a raised rib 195, which is positioned, sized and shaped to engage with a detent in the fluid housing component 300.

The delivery tube 110 and fluid lumens 120, 130 may be made of any materials, including polymeric materials or metallic materials. It is particularly desired that the fluid lumens be made of materials such as polyamides, polyurethanes, or other thermoplastics, although the lumens may be coated or treated with additional materials as desired. The needled cannula 140, 150 should be sufficiently stiff and sturdy so as to be capable of piercing a polymeric or elastomeric material when forced against that the polymeric or elastomeric material. The housing 160 is desirably a rigid polymeric material, such as polycarbonate. The delivery tube 110 may have any desired length, as appropriate for the clinical application including from about 4 cm to about 180 cm. Each fluid lumen 120, 130 may have any diameter desired, including about 0.03" to about 0.05", although will generally be selected in consideration of balancing and minimizing priming volume while maintaining suitable dispensing forces.

Figure 5:
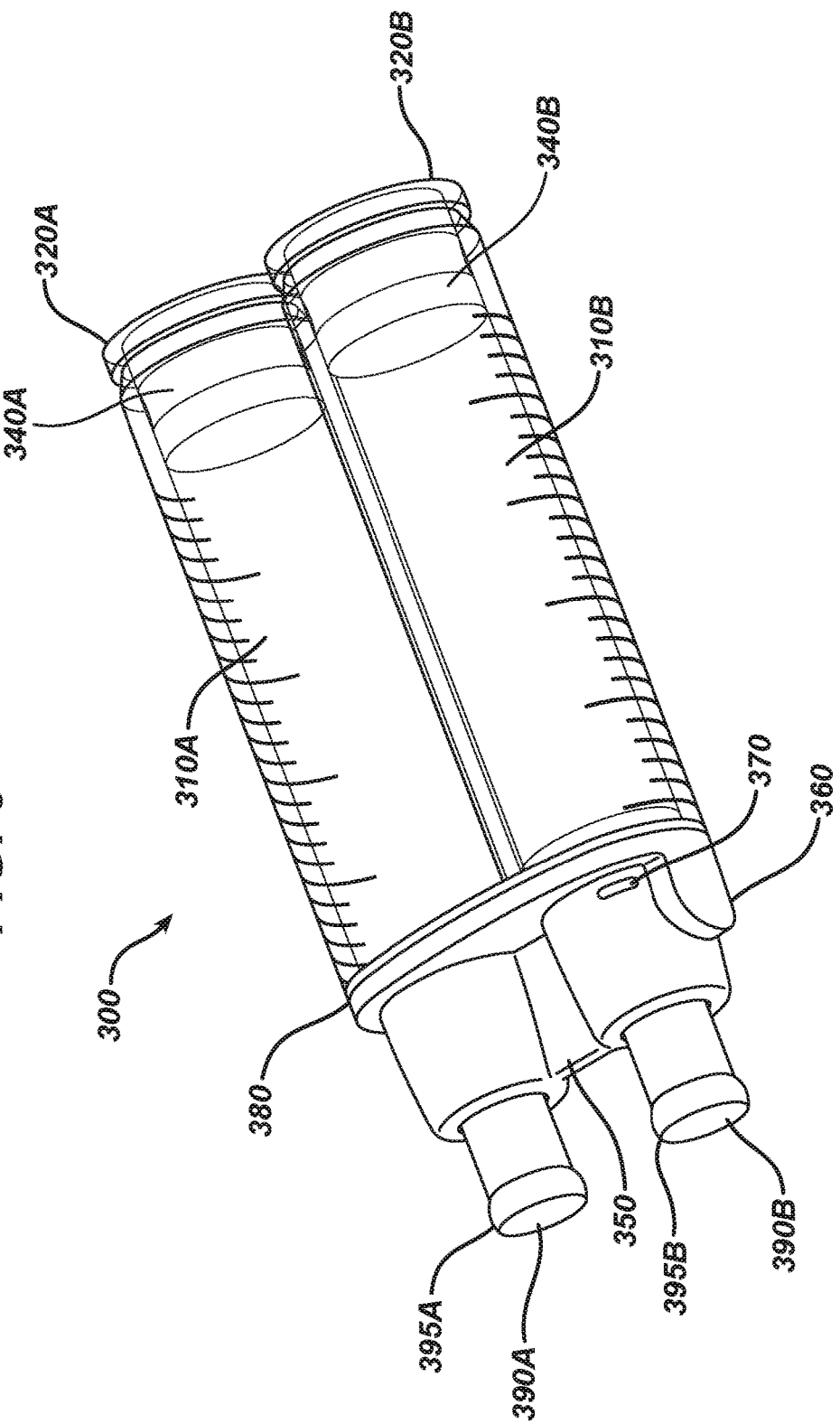
FIG. 5 is a close-up view of a fluid housing component with two barrels.
Figure 6:
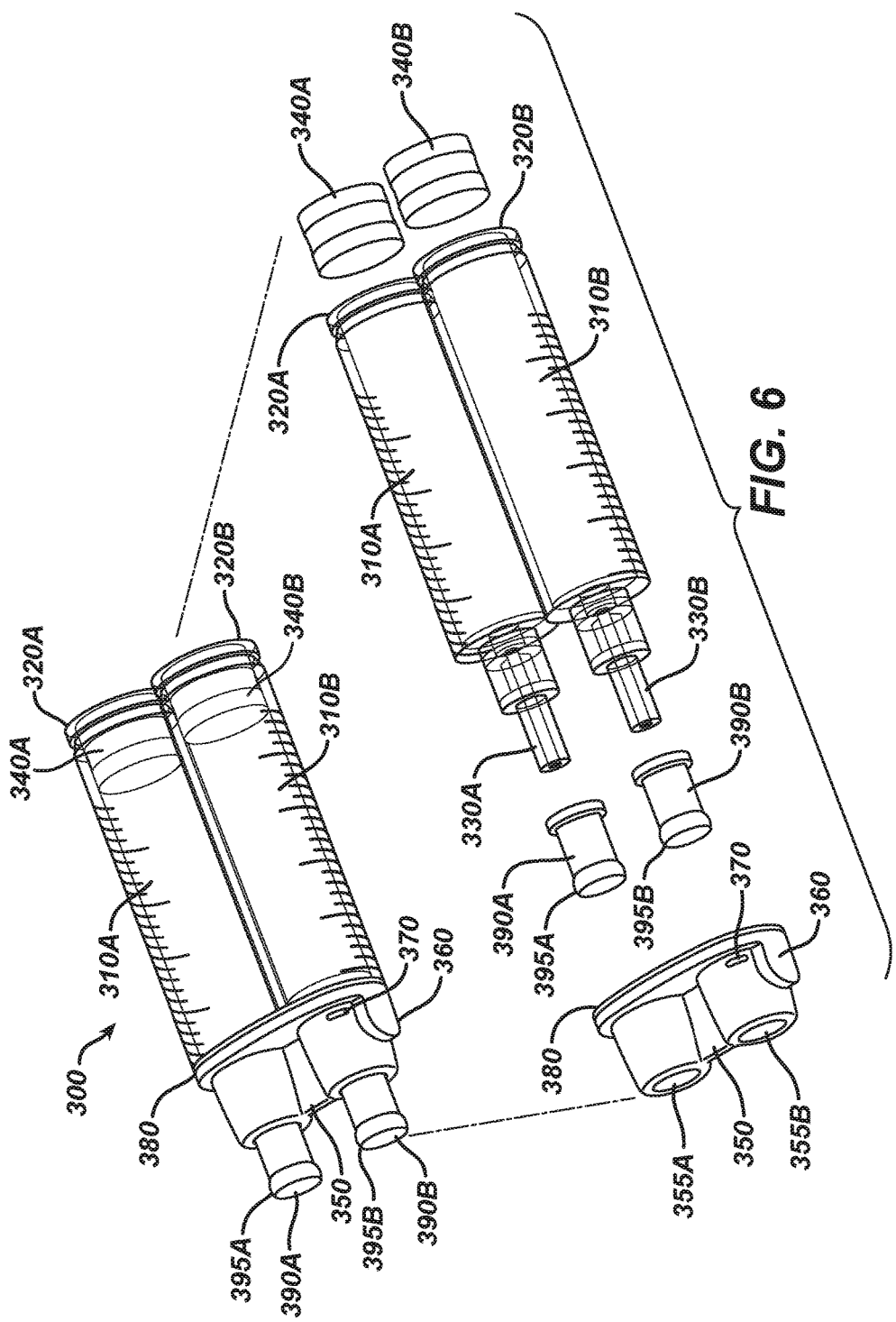
FIG. 6 is an expanded view of the fluid housing component of FIG. 5.

With reference to FIGS. 5 and 6, the fluid housing component 300 is described. The fluid housing component 300 includes at least one, and preferably two cylindrical barrels 310A, 310B each having an open interior running along the central axis of each barrel 310. The barrels 310A, 310B are aligned to be parallel to each other, with each central axis running parallel to each other. The barrels 310A, 310B should be substantially the same size, shape, and length, and may include one or more indicia thereon. The barrels 310A, 310B may be made of any material, including glass, plastic, metal, and combinations thereof. The barrels 310A, 310B may each have a different diameter (not shown), if desired, so that the mixing of the components contained in the barrels 310A, 310B may be performed in the volumetric ratio other than 1:1. It may be desired that the device and method described herein mix a greater volumetric amount of fibrinogen than thrombin. For example, the mixing may be performed in volumetric ratios of about 1:2, 1:3; or 1:4 (thrombin:fibrinogen). The mixing may be performed in a volumetric ratio of about 1:5 (first fluid:second fluid), which may include about one part of thrombin (or thrombin solution) mixed with about five parts of fibrinogen (or fibrinogen solution). Each "part" described herein is by volume.

As can be seen in FIG. 6, each barrel 310 is aligned in parallel configuration, but the barrels 310 need not be physically attached to each other. Each barrel 310 includes a proximal end 320 (also referred to as a "plunger-receiving end") and includes a distal end 330 (also referred to as a "dispensing end"). Each of the proximal end 320 and distal end 330 has an open interior, and the ends are in fluid connection with each other through the open central axis of the barrel 310. A separate, generally cylindrical piston 340 is provided for each barrel 310. The piston 340 is sized and shaped to be snugly but slidably fit within the interior of the barrel 310, and desirably has a polymeric or rubber elastomeric exterior circumference. The polymeric or rubber elastomeric exterior circumference is in contact with the circumference of the inside of a barrel 310, so as to act as a piston in a typical syringe-type assembly. Pushing the piston 340 through the center of the barrel 310 provides the necessary pressure to evacuate fluid materials from the inside of the barrel 310 out the dispensing end 330 of the barrel. The piston 340 may have a substantially flat proximal surface, and may have no rod or other pushing means secured or attached thereto as in typical syringe assemblies. When fluid materials are housed in the barrel 310, piston 340 is desirably fit into the barrel 310 such that the proximal end of the piston 340 is substantially flush with the proximal end 320 of the barrel 310. This flush fit aids in sterilization, as it reduces shadowing, stepped regions, and uneven surfaces of components.

The fluid housing component 300 desirably includes a bridge 350, which is a rigid component having a plurality of (at least two) open passageways 355A/B that are aligned in parallel with each other. The bridge 350 is sized and shaped to fit a portion of each barrel 310 so as to keep the barrels 310A/B in a secured position with respect to each other. The bridge 350 includes a second keyfit feature 360 that is sized and shaped to mate and engage with the first keyfit feature 190 of the applicator component 100. As seen in the Figures, the first keyfit feature 190 is depicted as a receiving region, and the second keyfit feature 360 is an extended region, but it is understood that the two may be reversed. The bridge 350 may include a detent 370, which is sized and shaped to mate with the raised rib 195 of the applicator component 100 and form a secured connection between the two components. A gasket 380 or other radial seal may be provided between the bridge 350 and the barrels 310A/B.

At the distal end 330 of each barrel 310 is provided a polymeric or rubber cap 390A/B, which is sized and shaped to fit snugly and securely over the open distal end 330 of each barrel 310. The cap 390 is to be secured to the distal end 330 of the barrel 310 in such a fashion that any material contained within a barrel 310 is secured in a leak-free environment. That is, the cap 390 secures the fluid material within the barrel 310. The cap 390 has a distal surface that is capable of being pierced with a needle. When the barrels 310 are secured in the bridge 350, the caps 390 are contained within the bridge 350. More specifically, one cap 390 is disposed within one of the open passageways 355 of the bridge 350. When two barrels 310 are used, first cap 390A is placed and secured within first open passageway 355A, and second cap 390B is placed and secured within second open passageway 355B.

When the delivery device 10 is assembled, the cap 390 is snugly fit within the open chamber 170 of the applicator component 100, thus providing a tight-fit seal and reducing the tendency of fluid material to leak once the cap 390 is pierced with the needled cannula (e.g., 140, 150) of the applicator component 100 and especially once the dispensing of fluid material is performed via advancement of the piston 340 within the barrel 310. To aid in forming a tight, leak-free seal, the cap 390 may include an outwardly extending radial rib 395, extending about and around the external circumference of the cap 390. The radial rib 395 is compressed against the interior side wall of the open chamber 170 when connected, forming a secure, fluid-tight seal and preventing leakage out of the chamber even if slight leaking occurs out from the opening in the cap.

It is desired that each of the parts of the assembled device 10 be connected in a gapless, fluid-tight configuration, so as to prevent or reduce the likelihood of accidental leakage of the fluid material(s) contained within any barrel 310 or during operation of the device. The use of seals, gaskets and tight configurations aids in securing the fluid materials.

In use, the keyfit engagement between applicator component 100 and fluid housing component 300 only allows the components 100, 300 to be secured to each other in one configuration. This proper assembly forces each needled cannula (e.g., 140) to be connected in a single orientation with a single barrel 310, and specifically into the pierced cap 390 on that barrel 310. This keyfit engagement ensures proper orientation and, importantly, proper piercing of the cap(s) 310 during use. This also allows for ease of replacing the components, in cases where the user wishes to replace the applicator component 100 or fluid housing component 300 mid-procedure.

Figure 7:
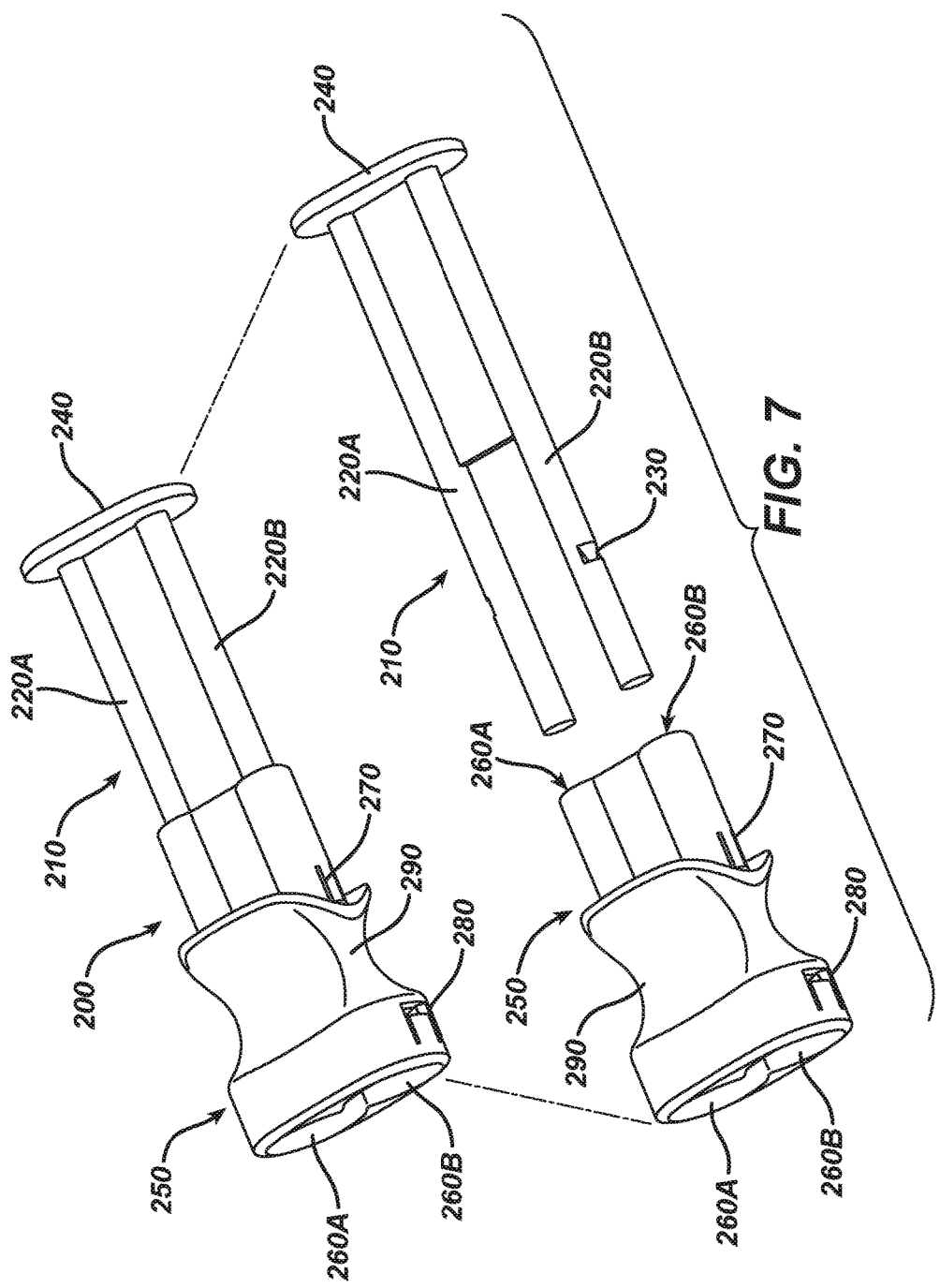
FIG. 7 is a close-up and expanded view of a plunger component.

FIG. 7 depicts a plunger component 200, which may be useful in the present invention. The plunger component 200 includes a plunger 210, which includes a plurality of pushing rods 220A/B, which may have any cross-sectional configuration, including cylindrical, square or diamond-shaped, or any other geometric cross-section. Desirably, there is one pushing rod 220 for every barrel 310 in the assembly 10. The pushing rods 220 may include one or more notches 230 on its outer surface, which may be used with a friction element so as to prevent inadvertent withdrawal of the plunger 210. The pushing rods 220 may be connected to each other at their proximal end via a depressor 240 to ensure depression of the rods 220 simultaneously. The depressor 240 may take any shape or configuration, and desirably is designed such that a user may place his or her thumb or fingers on the depressor 240 comfortably. The plunger component 200 includes a finger flange 250, which has a generally open interior and is sized and shaped to allow the pushing rods 220 to slidably move within its interior chambers 260A/B. The interior chambers 260A/B extend throughout the entire length of the finger flange 250 and hold the rods 220 in an aligned configuration.

The finger flange 250 may include an internal notch or friction element 270, which is disposed at a location selected to engage rods 120 such that motion of the rods is slightly restricted and cannot move under the influence of gravity alone. The finger flange further includes notch 230. The engagement of notch 230 and friction element 270 is such that the pushing rod 220 may be pushed distally but is restricted from being removed in the proximal direction, preventing rods 120 from being inadvertently detached from the finger flange. Finger flange 250 may also include at least one snap engagement means 280 at one or each interior chamber 260, which is designed to engage with a barrel 310, securing the barrel 310 in the interior chamber 260 when connected. Finger flange 250 may also include an ergonomic holder region 290 for ease of use. In the Figures, pushing rods 220A/B are not attached to pistons 340 A/B, thereby preventing movement of pistons in proximal direction if pushing rods 220 A/B are pulled in the proximal direction.

Figure 8:
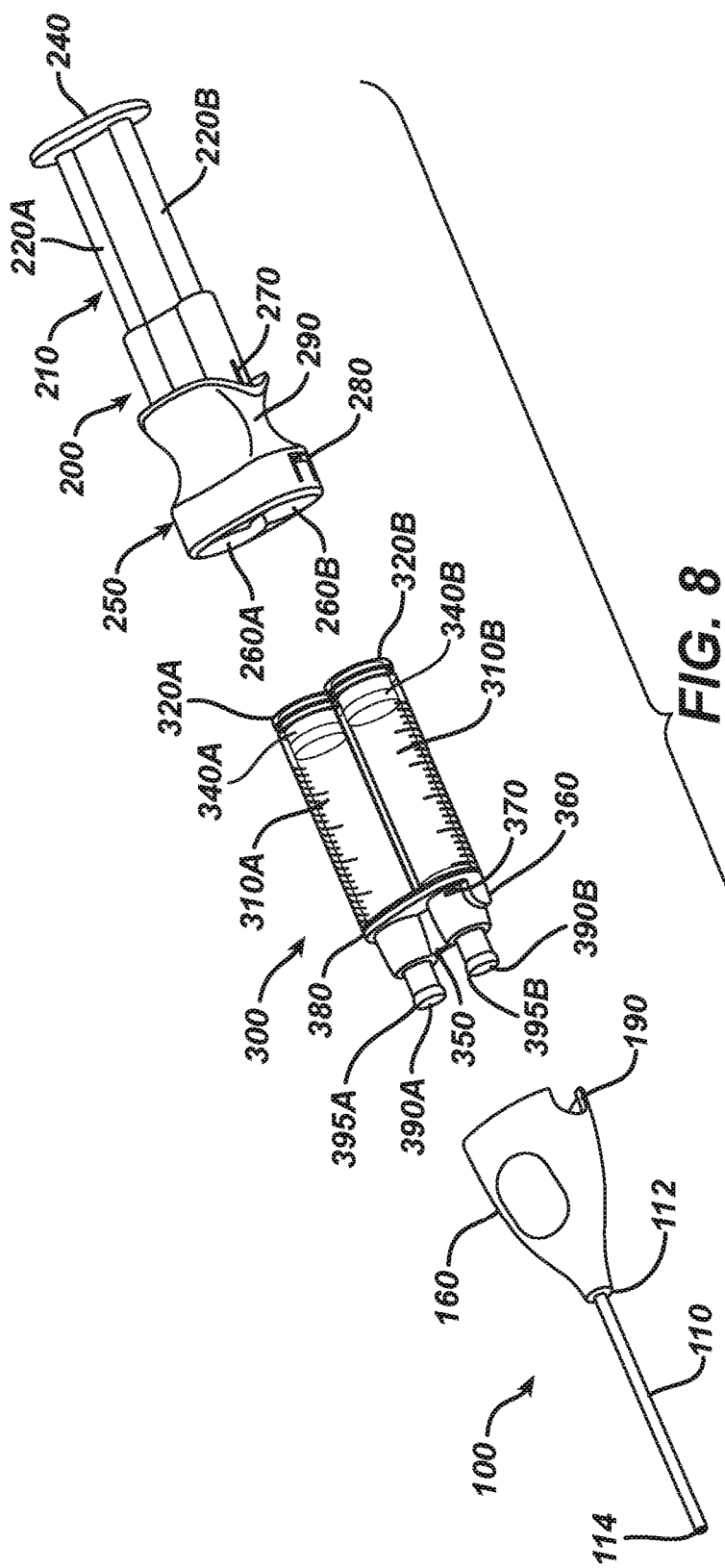
FIG. 8 is an expanded view of various components forming a delivery apparatus.

As can be seen in FIG. 8, the three components (100, 200, 300) of the assembled delivery device 10 are axially aligned with each other, such that the distal end of the fluid housing component 300 can be inserted into the proximal end of the applicator component 100, and the proximal end of the fluid housing component 300 can be inserted into the distal end of the plunger component 200. When each component is secured in this fashion, the various seals, friction fits and snap fits serve to maintain the completed delivery device assembly 10 in a substantially fluid-tight and secure configuration.

Figure 9:
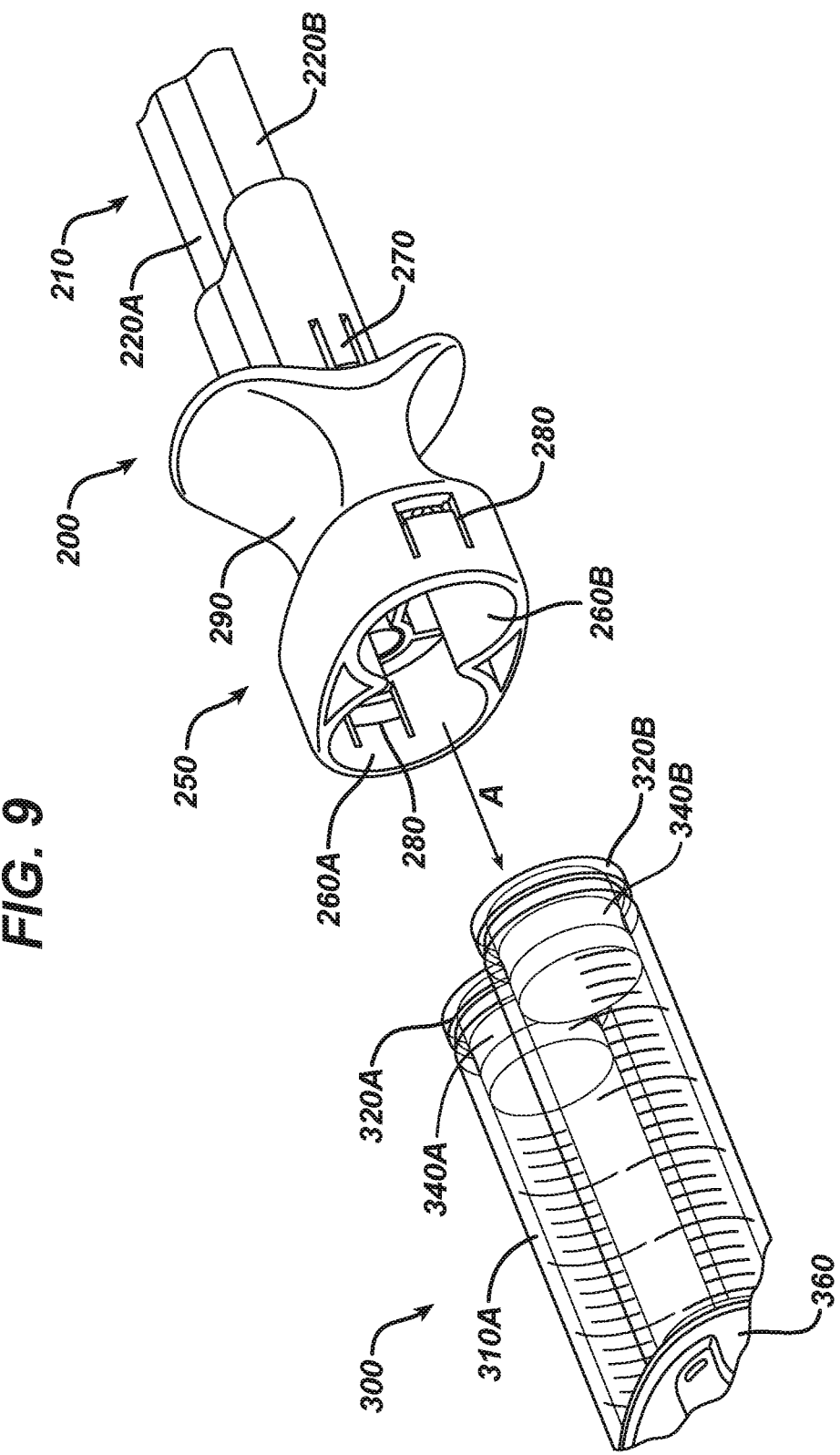
FIG. 9 is an expanded view of a plunger component and fluid housing component in unattached configuration.

As can be seen in FIG. 9, the proximal end 320 of each barrel 310 may be inserted into the distal end of the interior chamber 260 of the finger flange 250, and may be snapped or secured into place via engagement means 280. Given the alignment of the pushing rods 220 through the interior chambers 260, in this configuration, one pushing rod member 220 is capable of being pushed axially into the open central region of one barrel 310. In this fashion, the movement of a pushing rod 220 in the distal direction causes the pushing rod 220 to engage the proximal side of a piston 340, moving that piston 340 axially through the barrel 310, and thus forcing any fluid within the barrel 310 out the dispensing end 330 of the barrel 310. In FIG. 9, two barrels 310A/B are inserted into the plunger component 200, with a first barrel 310A inserted into a first interior chamber 260A and a second barrel 310B inserted into a second interior chamber 260B.

The use of pistons 340 and pushing rods 220 as separate components that are not secured or attached to each other, as well as the flush fit of the piston 340 in the barrel 310, provides an additional benefit as it serves to eliminate potential shadowing of the barrel assembly (e.g., barrel 310 and piston 340 contained therewithin), and further provides bearing/support surfaces to guide the plunger. In this configuration, the plunger component 200 is not actively secured or attached to a piston 340 with an undercut such that the piston 340 can be both advanced and retracted. In this unattached configuration, the pistons 340 can only be advanced (in the distal direction). Of course, it is understood that the lack of attachment of rods 220 with the pistons 340 may potentially allow free movement of the rods 220 in the proximal direction, and thus engagement of the friction element 270 with rods 120 may be useful in preventing inadvertent proximal movement of the plunger 210. Further, the friction element 270 provides a degree of force onto the pushing rod 220, such that exertion of some force (e.g., greater than mere gravity) by a user is required to push the plunger 210 in the distal direction.

FIG. 10 shows the insertion of the distal end 330 of each barrel 310 inserted into the applicator component 100, and more specifically into the housing 160. FIG. 10 shows a see-through, transparent or translucent housing 160, although it is understood that the housing 160 need not be transparent or translucent, and may be opaque or shaded. As can be seen, alignment of the applicator component 100 and fluid housing component 300 is achieved by aligning each keyfit component 190, 360, and securing the components in place via detent 370 and rib 195. The alignment due to the keyfit components 190, 360 ensures proper engagement and piercing of the caps 390. Further, securement via detent 370 and rib 195 provides secure engagement and also may provide tactile or audible feedback to a user when the components are snapped together. Any snap-fit or other securement means may be used in place of a detent 370 and rib 195 connection depicted in the Figures.

When a barrel 310 is inserted into the housing 160, the cap 390 is forced axially toward the distal end into open chamber 170, where it engages with needled cannula (e.g., 140). Due to the force imparted by inserting the barrel 310 into the housing 160, the needled cannula 140 pierces the cap 390, thus providing a fluid channel from the interior of the barrel 310 to the interior of the fluid lumen (e.g., 120). The number of barrels 310 inserted into the housing 160 should be equal to the number of open chambers 170 and therefore equal to the number of lumens and needled cannulas. The force required to pierce the cap 390 is not significant, but some degree of force is required to push the barrel 310 into the housing 160 and cause piercing by the needled cannula (140, 150).

As can be seen in FIG. 10, each cap 390 may include a radially extending rib 395 about its external circumference, which is pressed snugly against the interior surface of the open chamber 170. If used, the radially extending rib 395 forms a secure, fluid-tight seal, preventing fluid from being forced through the open chamber 170 and into the housing 160. Pressure caused by the seal of the rib 395 and open chamber 170 helps to reduce leakage through the cap, however, even if some fluid leaks through the cap (e.g., through the pierced region, around the outside of a needled cannula), the presence of the radial seal will prevent further leakage into the housing 160. A gap may be present between the far distal surface of the cap 390 and the interior of the open chamber 170, where the gap may securely contain any leaked fluid.

The present invention allows for the fluid or fluids to be filled into the fluid housing component 300 in a secure manner, with little risk of cross-contamination and without the need to subject the other components (including applicator component 100 and plunger component 200) to the fluids. Through the present invention, the applicator component 100 and plunger component 200 can be separately made and stored, and may be sterilized through traditional sterilization methods, including heat, chemical or radiation sterilization methods. They may be packaged or stored in sterile packaging until ready for use.

The fluid housing component 300 is a separate component including a plurality of barrels 310, desirably two barrels 310A and 310B. The barrels 310 may be individually filled with fluid materials, including biological material or other materials that are to be dispensed. A barrel 310 can be filled to the desired amount, and then sealed by inserting a piston 340 into the proximal end 320 of the barrel 310 and placing a cap 390 on the distal end 330 of the barrel 310. After filling with a desired amount of fluid, the piston 340 may be placed first, or the cap 390 may be placed first, or each may be placed simultaneously. As noted above, the piston 340 is desirably placed such that the proximal end of the piston 340 is substantially flush with the proximal end 320 of the barrel 310, creating a proximal end assembly that has little to no ridges, gaps, steps or other such uneven features. The barrel 310 may be sterilized prior to filling if desired.

In a method of the present invention, a first barrel 310A may be filled with a first reactive fluid composition, and a second barrel 310B may be filled with a second reactive fluid composition, where the first and second reactive fluid compositions react with each other to form a third composition. For example, the third composition may be a fibrin sealant, or alternatively, it may be an epoxy or acrylate. In instances where the third composition is a fibrin sealant, the first reactive composition may be fibrinogen and the second reactive composition may be thrombin. The fluids used in the present invention may be a liquid, gel, suspension, gas, or combinations thereof. Each barrel 310 is filled to a desired amount of material, and each barrel 310 is then secured with a piston 340 and a cap 390. If more than one barrel 310 is to be used, each barrel 310 may additionally be secured together in a substantially parallel configuration with a bridge 350.

Again, it may be desired that the various components, excluding sensitive materials such as biological fluids, be pre-sterilized using conventional means prior to filling with fluid materials. Such conventional sterilization means include, for example, heat, radiation, steam, chemical or other treatment. The subsequent filling, sealing, and packaging of the fluid housing component 300 desirably is conducted in an aseptic environment such as an isolator, so as to avoid contamination. One of the benefits of the present invention is that the device may be further sterilized after filling is completed, even if the material to be filled is a sensitive biological material. In such instances, the filled fluid housing component 300 (which has been sealed with piston 340 and cap 390) may be exposed to a treatment, such as by exposure to radiation energy to further sterilize the component 300 or its external surfaces, with no detrimental effects of the sterilization treatment upon the biological component contained therein. The radiation energy may include a low energy electron beam, which provides additional sterilization to the exterior of the component 300, avoiding possible contamination that occurred during the assembly process.

The geometry and materials of components of the fluid housing component 300 are selected to assure that all exposed surfaces can be exposed to the radiation energy. Furthermore, use of elastomeric components or sealing features (such as gasket 380) assures intimate seals between components, eliminating cracks and crevasses shielded from radiation energy that might harbor contamination accessible to fluids in the surgical field. Specifically, the seal from barrel 310 to bridge 350, the seal created by cap 390, and the seal created at the piston 340 on the interior of the barrel 310 all aid in preventing damage or contamination of the fluids within the barrel 310. It may be desired that the wall of the barrel 310 has a thickness of about 0.06", which is sufficient to prevent or reduce the likelihood of energy being transmitted through the wall and contact the fluid contained therein.

Once the fluid housing component 300 is filled and sealed, it can be packaged and subjected to surface sterilization prior to passing out of the isolator, where it can be stored and ultimately provided to an end user. Each barrel 310 may be stored separately, or a plurality of barrels 310 may be secured together via bridge 350 and stored as an assembly. If desired, the fluid housing component 300 may be stored in a refrigerated or controlled temperature environment, if the fluid materials housed therein require such temperature control. The fluid housing component 300 may be provided to an end user by itself, or it may be provided concurrently with the applicator component 100 and/or plunger component 200. For example, the three components (100, 200, 300) may be sold as a kit to be used by a user, and the kit may include instructions for use if desired. Alternatively, one or two of the components may be provided to a user separately.

The present invention relates to methods of using the device described above. Each of the three main components of the modular device 10 (the "main components" is defined as including the applicator component 100, plunger component 200 and fluid housing component 300) may be provided to an end user at the same time or they may be provided separately. An end user includes any individual or institution that seeks to deliver a fluid, including biological fluids or other fluids described above. The end user may be, for example, a medical professional, and the resulting combination or mixture to be delivered may be fibrin (which rapidly forms upon mixing of two fluids: fibrinogen and thrombin). Desirably, each of the three main components is sterilized and maintained in a sterile packaging until ready for use by an end user. The fluid housing component 300 is provided to an end user in a filled state, e.g., where each barrel 310 includes a desired amount of fluid material. For example, the fluid housing component 300 may include two barrels, 310A and 310B, where first barrel 310A includes a desired amount of thrombin and second barrel 310B includes a desired amount of fibrinogen. The barrels 310A/B are sealed as described above and sterilized as described above, and secured to each other by inserting each barrel 310A/B into a bridge 350. Providing sterilized and pre-filled barrels 310 is useful because it allows quick, safe and easy use by an end user in a sterile environment with little risk of contamination.

Once the end user has the three main components, each main component can be transferred to a sterile field. The applicator component 100 is secured to the fluid housing component 300, as described above, and the plunger component 200 is secured to the fluid housing component 300, as described above. The order of assembly is not critical, and either the applicator component 100 or the plunger component 200 may be secured first. As the fluid housing component 300 is secured into the housing 160 of the applicator component 100, each needled cannula 140, 150 engages one of the caps 390, piercing the cap 390 and providing a fluid connection between the fluid lumens 120, 130 and the interior of the barrel 310 with which it is connected.

Once assembled, the end user places the device 10 in a dispensing location, where the distal end 114 of the delivery tube 110 is at or near the target delivery site. For example, the target delivery site may be the site of a wound or surgical site to be sealed. The end user holds the delivery device 10 in his or her hands, and pushes the depressor 240 in the distal direction. Pushing the depressor 240 moves the pushing rods 220 in the distal direction, where each pushing rod 220 engages the proximal end of a piston 340, forcing the piston 340 distally through the inside of a barrel 310. As noted above, since there is no attachment between the pushing rod 220 and piston 340, the piston 340 can only be pushed in the distal direction, and cannot be withdrawn by the pushing rod 220 in the proximal direction. Further, given the tight seal created around the outer circumference of the piston 340, pushing the piston 340 in the distal direction forces fluid from the inside of the barrel 310 distally, where the fluid can be fed through the needled cannula (e.g., 140) and through fluid lumen (e.g., 120). Although desirably there is no fluid leakage through the pierced portion of the cap 390, it is possible that some fluid leakage may occur. For this reason, use of a seal formed by the sidewall of the open chamber 170 and a raised rib portion 395 about the circumference of the cap 390 is useful, but not required.

As pressure is exerted on the piston 340, the fluid travels through the fluid lumen (e.g., 120), and out the distal end 114 of the delivery tube 110. If a first fluid is contained in a first barrel 310A and a second fluid is contained in a second barrel 310B, pushing the depressor 240 pushes a first piston 340A and second piston 340B through first barrel 310A and second barrel 310B, respectively. The first fluid travels through first needled cannula 140, and through first fluid lumen 120, while the second fluid simultaneously travels through second needled cannula 150 and second fluid lumen 130. Each of the first and second fluids is dispensed through the distal end 114 of the delivery tube 110 simultaneously, where they are combined to form the ultimate reactive product. If the first fluid is thrombin and the second fluid is fibrinogen, the simultaneous dispensing and mixing results in a fibrin sealant. The end user can dispense as much or as little fluid as desired, and may end dispensing of the fluids by halting the exertion of pressure on the depressor 240. The mixing of the first fluid and the second fluid may also be performed within the delivery tube, within the applicator component, or in a specialized mixing tip attached to the delivery tube (not shown). The various components of the above-described invention can be prepared separately, packaged separately and stored separately until time of use. The invention allows for a safe, effective means of providing a delivery assembly which is capable of being sterilized while limiting risk of cross-contamination. The snap-fit engagement of the components allows for proper assembly by the end user without added steps or hassle and without risk of improper assembly. The alignment of the needled cannulas and the caps provides for accurate piercing of the caps, allowing entry of a fluid lumen into the interior of a barrel and therefore providing a suitable fluid engagement of the components. Further, given the ease and simplicity of attaching and detaching the components, if a component needs to be replaced during use, it can easily be removed and replaced. For example, if the end user has dispensed all of the fluids in the barrels, the end user need only detach the fluid housing component and replace it with a new, filled fluid housing component. This can be achieved quickly, safely and easily.

The present invention may include any of the applicator component 100, fluid housing component 200, and/or plunger component 300, including any of the variations and components described with reference to each particular component (100, 200, 300).

The invention claimed is:

1. An apparatus for delivery of a biological fluid, comprising:
   a. an applicator component, said applicator component comprising:
      i. a housing;
      ii. first and second open chambers within said housing, each open chamber having generally cylindrical sidewalls and being aligned such that the central axes of each open chamber are parallel with each other; and
      iii. first and second fluid lumens, each fluid lumen having an insertion end and a delivery end, said insertion end of each fluid lumen comprising a needled cannula disposed within one of said open chambers;
   b. a fluid housing component, comprising:
      i. at least two cylindrical barrels, each having an open interior extending between a dispensing end and a plunger receiving end;
      ii. at least two elastomeric caps each comprising a raised circumferential rib, wherein a first elastomeric cap of the at least two elastomeric caps is fit onto the dispensing end of a first cylindrical barrel of the at least two cylindrical barrels, wherein the raised circumferential rib of the first elastomeric cap is sized and shaped to be snugly fit within one of said open chambers in said housing by abutting the cylindrical sidewall of said open chamber to form a water-tight seal, wherein the first cylindrical barrel and the first elastomeric cap are configured to actuate as a unit to selectively couple and decouple with the applicator component;
      iii. at least two pistons, each having a generally cylindrical configuration, with each having a sealing surface on an outer circumference and a generally flat proximal surface;
      iv. a bridge having an open interior, which fits securely on at least one of the dispensing ends of said at least two cylindrical barrels; and
   c. a plunger component, comprising:
      i. at least two pushing rods, each having a first end and second end, wherein the first end of a first pushing rod of the at least two pushing rods may be inserted into the plunger receiving end of the first cylindrical barrel of the at least two cylindrical barrels;
      ii. an open flange component through which said pushing rods may be slidably inserted; and
      iii. a securement feature to secure the dispensing end of said barrels in the open flange component.

2. The apparatus of claim 1, wherein said housing of said applicator component comprises a first keyfit region, said bridge comprises a second keyfit region, and said first keyfit region and said second keyfit region are sized and shaped to mate with each other.

3. The apparatus of claim 1, wherein said applicator component and said fluid housing component can be secured to each other by inserting said fluid housing component into the housing of the applicator component.

4. The apparatus of claim 3, wherein insertion of the fluid housing component into the housing of the applicator component aligns the needled cannula of the first fluid lumen with the open interior of the first cylindrical barrel by piercing the first elastomeric cap.

5. The apparatus of claim 1, wherein a first piston of the at least two pistons is fit within the first cylindrical barrel so as to form a sealed fit about the outer circumference of the first piston and an interior wall of the first cylindrical barrel.

6. The apparatus of claim 5, wherein the generally flat proximal surface of said first piston is aligned in a substantially flush configuration with the plunger receiving end of the first cylindrical barrel into which the first piston is disposed.

7. The apparatus of claim 1, wherein when said plunger component is secured to said fluid housing component, a first end of one of said pushing rods contacts the proximal surface of one of said pistons.

8. The apparatus of claim 1, wherein a biological fluid is placed within the first cylindrical barrel, wherein said biological fluid is contained within the first cylindrical barrel due to a first seal and a second seal, wherein the first seal is created by a first piston and an interior surface of the first cylindrical barrel, wherein the second seal is created by the dispensing end of the first cylindrical barrel and the first elastomeric cap secured to said first cylindrical barrel.

9. A method of dispensing at least two biological fluids simultaneously, comprising the steps of:
   a. providing an applicator component, said applicator component comprising:
      i. a housing;
      ii. first and second open chambers within said housing, each open chamber having generally cylindrical sidewalls and being aligned such that the central axes of each open chamber are parallel with each other; and
      iii. first and second fluid lumens, each fluid lumen having an insertion end and a delivery end, said insertion end of the first fluid lumen comprising a first needled cannula disposed within the first open chamber and the insertion end of the second fluid lumen comprising a second needled cannula disposed within the second open chamber;
   b. providing a fluid housing component, comprising:
      i. first and second cylindrical barrels each having an open interior extending between a dispensing end and a plunger receiving end;
      ii. first and second elastomeric caps, wherein the first elastomeric cap is fit onto the dispensing end of the first cylindrical barrel and the second elastomeric cap is fit onto the dispensing end of the second cylindrical barrel, wherein the first elastomeric cap comprises a first raised circumferential rib;
      iii. first and second pistons each having a generally cylindrical configuration, with a sealing surface on an outer circumference and a generally flat proximal surface, the first piston being placed within the plunger receiving end of the first barrel and second piston being placed within the plunger receiving end of the second barrel;
      iv. a bridge having an open interior, sized and shaped to receive the dispensing ends of the first and second cylindrical barrels and maintain the first and second cylindrical barrels in a substantially parallel configuration;
   c. providing a plunger component, comprising:
      i. first and second pushing rods each having a first end and second end, each sized such that the first end of each pushing rod may be inserted into the plunger receiving end of a respective cylindrical barrel from the first and second cylindrical barrels;

ii. an open flange component through which said pushing rods may be slidably inserted; and
iii. a securement feature to secure the dispensing end of said first and second barrels in the open flange component;
d. securing said applicator component to said fluid housing component by actuating the fluid housing component relative to the applicator component such that the first cylindrical barrel and the first elastomeric cap actuate together relative to the applicator component, such that the first raised circumferential rib abuts against the first generally cylindrical sidewall of the first open chamber in order to form a first fluid-tight seal, and such that the first needled cannula pierces the first elastomeric cap and the second needled cannula pierces the second elastomeric cap;
e. securing said plunger component to said fluid housing component; and
f. depressing said pushing rods, such that the first pushing rod moves the first piston in the distal direction through the first barrel and the second pushing rod moves the second piston in the distal direction through the second barrel, thereby forcing a first biological fluid through the first fluid lumen and a second biological fluid through the second fluid lumen.

10. The method of claim 9, wherein the delivery ends of each lumen are located substantially adjacent to each other, such that dispensing of said first and second biological fluids simultaneously causes mixing of said first and second biological fluids at the area of said delivery ends.

11. The method of claim 9, wherein the fluid housing component is subjected to an electron beam processing step after said first and second fluid components are disposed within the first and second barrels.

12. The method of claim 9, wherein the second elastomeric cap includes a second raised circumferential rib, wherein the second raised circumferential rib is configured to abut against a second generally cylindrical sidewall of the second open chamber in order to form a second fluid tight seal.

13. A kit comprising the applicator component, fluid housing component and plunger component of claim 9.

14. The kit of claim 13, wherein said fluid housing component comprises a first biological component within the first cylindrical barrel and a second biological component within the second cylindrical barrel.

15. A fluid housing cartridge for use in a modular delivery device, comprising:
a. at least two cylindrical barrels, each having an open interior extending between a dispensing end and a plunger receiving end;
b. at least two elastomeric caps, wherein a first elastomeric cap of the at least two elastomeric caps is fit onto the dispensing end of a first cylindrical barrel of the at least two cylindrical barrels, wherein the first elastomeric cap comprises a raised circumferential rib;
c. at least two pistons, each having a generally cylindrical configuration, with a sealing surface on an outer circumference and a generally flat proximal surface, a first piston of the at least two pistons being placed into the plunger receiving end of the first cylindrical barrel;
d. a bridge defining a first lumen, wherein the bridge fits securely on the dispensing end of said at least two cylindrical barrels so as to hold said at least two cylindrical barrels in a substantially parallel configuration, wherein the first elastomeric cap extends distally past the bridge through the first lumen.

16. The fluid housing cartridge of claim 15, wherein said bridge includes a keyfit feature at a distal end of the bridge, said keyfit feature shaped and sized to mate with a keyfit feature of an applicator component.

17. The fluid housing cartridge of claim 15, wherein the first piston is placed within the open interior of the first cylindrical barrel such that the generally flat proximal surface of the first piston is substantially flush with a proximal end of the first cylindrical barrel.

* * * * *